United States Patent [19]

Machemer et al.

[11] Patent Number: 5,609,602

[45] Date of Patent: Mar. 11, 1997

[54] OSCILLATORY COUPLING FOR SURGICAL INSTRUMENTS AND METHODS OF IMPARTING OSCILLATORY MOTION THERETO

[75] Inventors: Robert Machemer, Durham, N.C.; Dyson Hickingbotham, Marietta, Ga.; Brian Dodge, Durham, N.C.

[73] Assignee: Duke University, Durham, N.C.

[21] Appl. No.: 698,918

[22] Filed: Aug. 16, 1996

Related U.S. Application Data

[63] Continuation-in-part of Ser. No. 486,575, Jun. 7, 1995, abandoned.

[51] Int. Cl.$^6$ .................................................. A61B 17/32
[52] U.S. Cl. ........................... 606/171; 606/178; 606/159
[58] Field of Search ...................................... 606/170, 171, 606/159, 166, 178; 403/345, 374; 30/208, 163, 151; 83/575, 576

[56] References Cited

U.S. PATENT DOCUMENTS

| | | | |
|---|---|---|---|
| 3,978,862 | 9/1976 | Morrison | 606/178 |
| 5,269,794 | 12/1993 | Rexroth | 606/170 |
| 5,376,078 | 12/1994 | Dinger, III et al. | 606/170 |

*Primary Examiner*—Michael Buiz
*Assistant Examiner*—Kevin Truong
*Attorney, Agent, or Firm*—Nixon & Vanderhye P.C.

[57] ABSTRACT

Rotary oscillatory coupling includes a pair of opposed hubs which are independently rotatable about a common axis. Pairs of permanent magnets are provided in the opposed faces of the hubs. The proximal hub is continuously rotated in a selected rotational direction by a suitable motor. During a portion of the proximal hub's rotation, the distal hub will concurrently be rotated by virtue of the magnetic field interaction that occurs between the magnet pairs. The distal hub is, however, prevented from rotating a complete cycle by virtue of a mechanical stop. Upon encountering the mechanical stop, the rotation direction of the distal hub will be reverse to that of the continuously rotating proximal hub. When the magnets of the proximal and distal hubs again are in proximity to one another, the distal hub will then experience another reversal of rotation direction so that it rotates in the same direction as the proximal hub. This functional process repeats itself during subsequent rotational cycles to cause the distal hub to undergo high frequency oscillations.

33 Claims, 3 Drawing Sheets

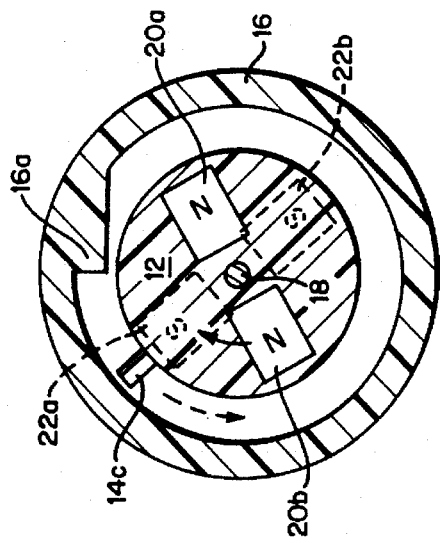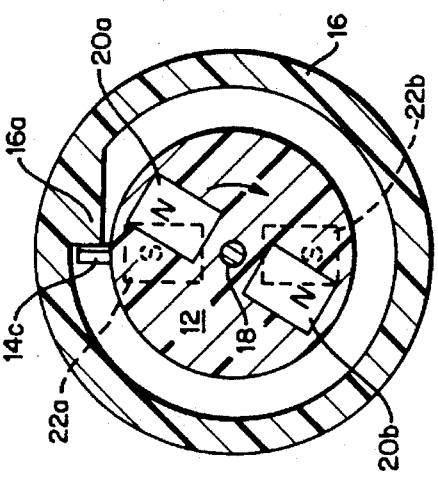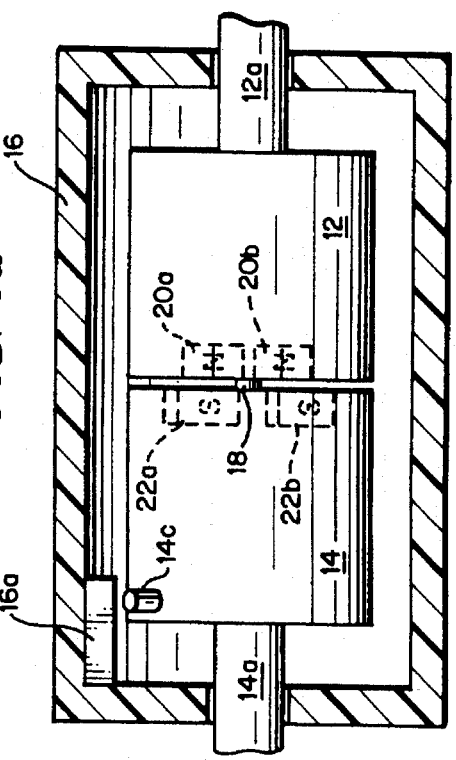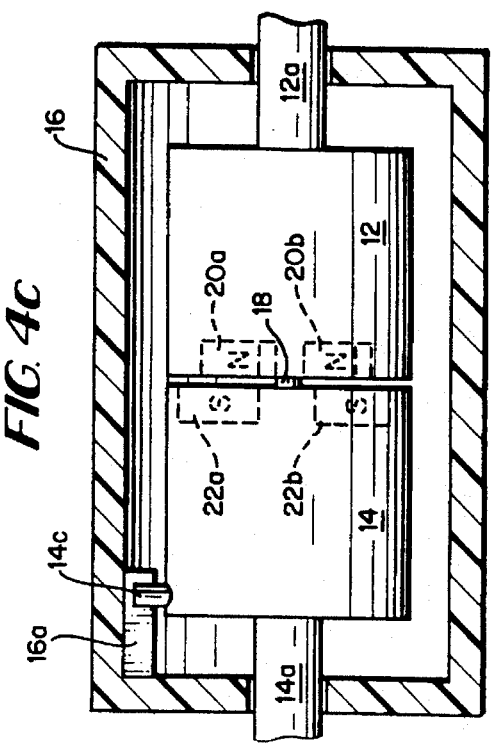

OSCILLATORY COUPLING FOR SURGICAL INSTRUMENTS AND METHODS OF IMPARTING OSCILLATORY MOTION THERETO

CROSS REFERENCE TO RELATED APPLICATION

This application is a continuation-in-part of commonly owned U.S. application Ser. No. 08/486,575 filed on Jun. 7, 1995, now, abandonment on Nov. 1, 1996 the entire content of which is expressly incorporated hereinto by reference.

FIELD OF INVENTION

The present invention generally relates to couplings for imparting oscillatory motion to a distal element, such as a surgical instrument. In preferred forms, the present invention is embodied in a coupling for surgical instruments (e.g., ophthalmic microsurgical instruments for lens removal) so as achieve high frequency rotary (angular) oscillation.

BACKGROUND AND SUMMARY OF THE INVENTION

In ophthalmic microsurgery, such as lens removal, instruments are used with either horizontal or axial oscillatory movements. High frequency rotary (angular) oscillation to achieve lens destruction is not presently available. Furthermore, conventional horizontal or axial oscillatory instruments employing piezoelectric technology tend to create heat during operation which can damage ocular tissues. The very high frequency of these conventional oscillatory surgical instruments also can cause indirect damage to adjacent ocular tissues.

Therefore, what has been needed in this art is relatively low frequency rotary oscillatory coupling which would then be especially adapted for use with surgical instruments, particularly instruments employed in ophthalmic microsurgery. It is towards providing such a need that the present invention is directed.

Broadly, the present invention relates to a rotary oscillatory coupling and method of imparting rotary oscillatory movement by means of repetitive rotational direction reversals caused by the interactive influence of respective magnetic fields of positionally opposed permanent magnets. More specifically, the coupling of this invention includes a pair of independently rotatable hubs which carry paired permanent magnets of either opposite or like poles. One of the hubs is continuously rotated so that the magnetic field of the magnet it carries will cooperatively interact with the magnetic field of the magnet carried by the other hub and thereby cause the other hub to rotate. The other hub is, however, prevented from rotating a complete turn which thereby causes rotation direction reversal. Upon coming under the influence of the magnet in the continuously rotated hub, therefore, the other hub will again reverse its rotation direction. In such a manner, oscillatory rotary motion is imparted to the other hub.

In particularly preferred forms, the invention is embodied in an assembly for coupling a motor to a surgical instrument (e.g., for ophthalmic microsurgery such as lens removal) so as to achieve high frequency rotary (angular) oscillation. The coupling includes a pair of opposed hubs which are independently rotatable about a common axis. At least one pair of magnets is provided in the opposed faces of the hubs. The proximal hub is continuously rotated in a selected rotational direction by means of a suitable motor.

During a portion of the proximal hub's rotation, the distal hub will concurrently be rotated under influence of the magnetic field of the permanent magnet located in the proximal hub. The distal hub is, however, prevented from rotating a complete cycle by virtue of a mechanical stop. Upon encountering the mechanical stop, the distal hub will become magnetically "uncoupled" (to be defined below) from the leading magnet of the proximal hub thereby causing the distal hub to reverse its rotational direction compared to the proximal hub. When the magnets of the proximal and distal hubs again are positioned such that their respective magnetic fields interact(i.e., magnetically "coupled", to be defined below), the distal hub will again experience another reversal of rotation direction. This functional process repeats itself during subsequent rotational cycles to cause the distal hub to undergo high frequency oscillations.

Further aspects and advantages of this invention will become more clear from the following detailed description of the preferred exemplary embodiments thereof.

BRIEF DESCRIPTION OF THE DRAWINGS

Reference will hereinafter be made to the accompanying drawings wherein like reference numerals throughout the various FIGURES denote like structural elements, and wherein;

FIGS. 3a through 3d are sequential latitudinal cross-sectional views of the coupling according to this invention depicting various states of its rotary cycle; and FIGS. 4a through 4d are sequential longitudinal cross-sectional views of the coupling according to this invention which respectively correspond to the various states of the rotary cycle shown in FIGS. 3a–3d.

DETAILED DESCRIPTION OF THE PREFERRED EXEMPLARY EMBODIMENTS

Figure 1:
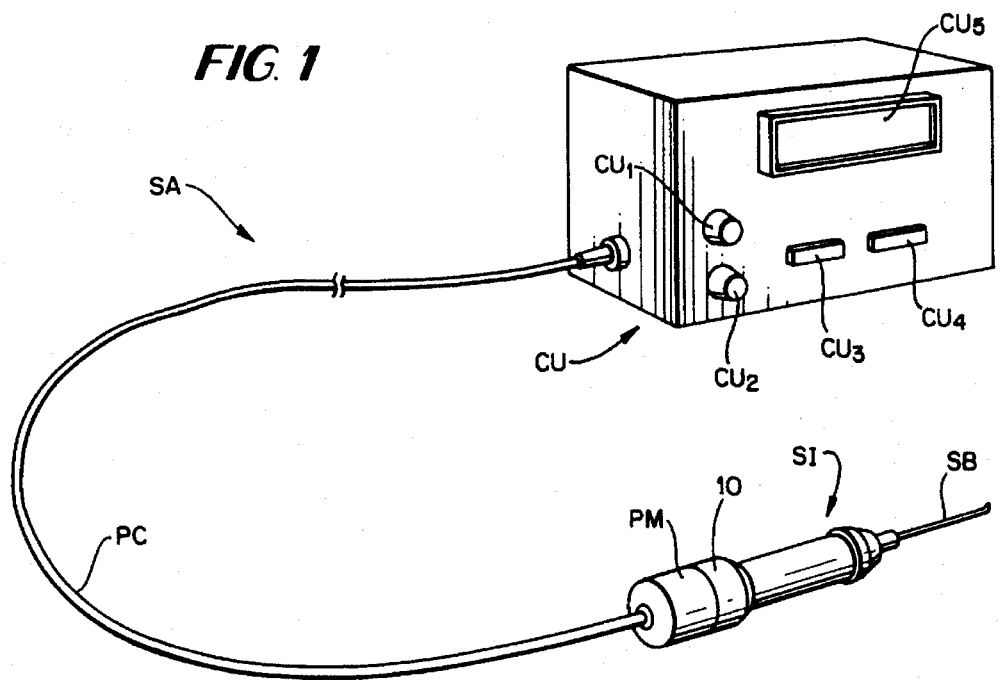
FIG. 1 is a schematic perspective view of a surgical apparatus which may employ the rotary oscillatory coupling according to the present view.

Accompanying FIG. 1 schematically represents a surgical assembly SA having a hand-held surgical instrument SI which employs the coupling unit 10 according to this invention. The assembly SA also includes a control unit CU which provides data and/or power via cord PC to a high speed precision motor PM coupled operatively to the coupling unit 10 of this invention. Alternatively, the precision motor PM and/or coupling unit 10 can be housed within the control unit CU, in which case rotary motion is transferred to the surgical instrument via a conventional flexible drive shaft routed within the cord PC. In use, the controls $CU_1$–$CU_4$ of the control unit CU may be manipulated by the attending physician with data being displayed on the display unit $CU_5$ (e.g., LED or LCD display).

Figure 2:
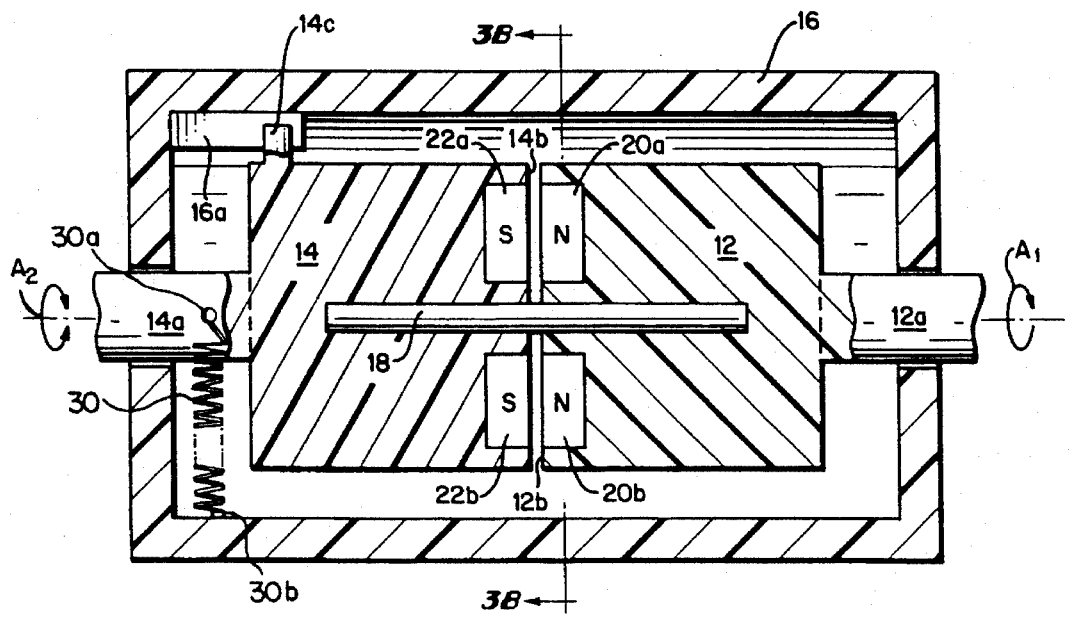
FIG. 2 is a schematic cross-sectional elevational view of the coupling according to this invention.

The structural components of the coupling unit 10 according to this invention are depicted schematically in accompanying FIG. 2. As is shown, the coupling unit 10 includes proximal and distal hubs 12, 14 each of which is mounted in opposed coaxial relationship to one another within the coupling housing 16 via shafts 12a, 14a, respectively. A rigid support shaft 18 coaxially joins the hubs 12, 14 to one another so as to allow each hub 12, 14 to independently rotate about the common axis of shaft 18.

Pairs of mutually attracting (i.e., oppositely poled) magnets 20a, 20b and 22a, 22b are provided in the opposed faces 12b, 14b of the hubs 12, 14, respectively. As will be described in greater detail below, the magnet pairs 20a, 20b and 22a, 22b couple the hubs 12, 14 to one another so that the rotation of hub 12 serves to drive the hub 14 throughout a portion of the latter's rotational cycle. In other words, the magnet pairs 20a, 20b and 22a, 22b serve to magnetically couple the hubs 12 and 14 so that they rotate concurrently with one another throughout at least a portion of their rotational cycle. The distal hub 14, however, is provided with a radially extending boss 14c which contacts a stop member 16a extending radially inwardly from the housing 16.

The shaft 12a is connected operatively to the drive shaft DC so that the hub 12 is responsively rotated (arrow $A_1$) by the precision motor (not shown) within the control unit CU. The shaft 14a, on the other hand, is coupled operatively to the surgical blade SB (see FIG. 1) of the surgical instrument SI. In such a manner, the rotary oscillation (arrow $A_2$) of the hub 14 is transferred to the surgical blade SB.

The operation of the coupling 10 according to this invention is shown in greater detail in accompanying FIGS. 3a–3d and FIGS. 4a–4d. In this regard, during a portion of the rotational cycle (due to the motorized rotational input to shaft 12a of hub 12), each of the proximal and distal hubs 12, 14, respectively, will be rotated in unison by virtue of the magnetic coupling that is present between the magnet pairs 20a, 20b and 22a, 22b (see FIGS. 3a and 4a). The distal hub 14 is, however, prevented from rotating a complete cycle by virtue of the contact which ultimately ensues between the boss 14c and the stop 16a (see FIGS. 3b and 4b).

With rotation of the distal hub stopped by contact between the boss 14c and stop member 16a, the proximal hub will meanwhile continue to rotate (i.e., since the proximal hub 12 is continuously driven by the motor (not shown) within the control unit CU so as to rotate in the direction of arrow $A_1$ as described previously). Because of this continuous rotation of the proximal hub 12, the magnet pairs 20a, 20b and 22a, 22b will become "uncoupled" as shown in FIGS. 3c and 4c.

Figure 3B:
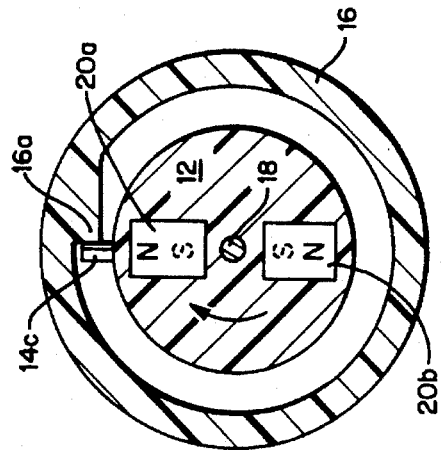
Figure 3A:
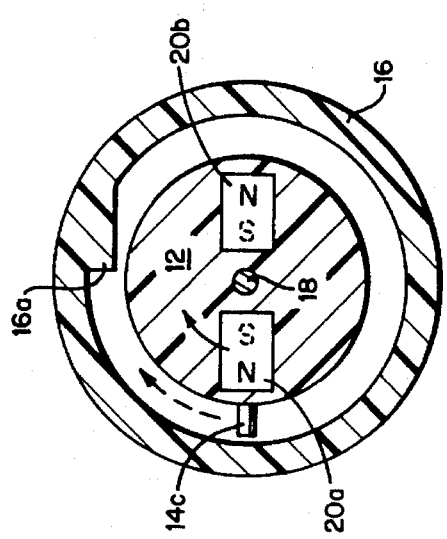
Figure 4B:
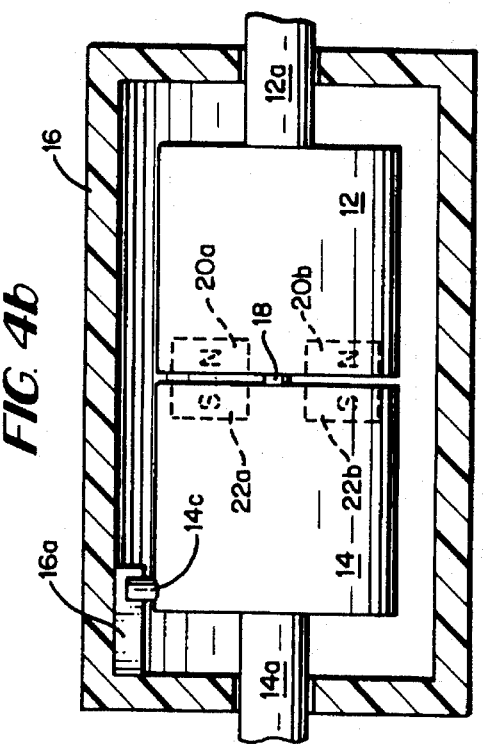
Figure 4A:
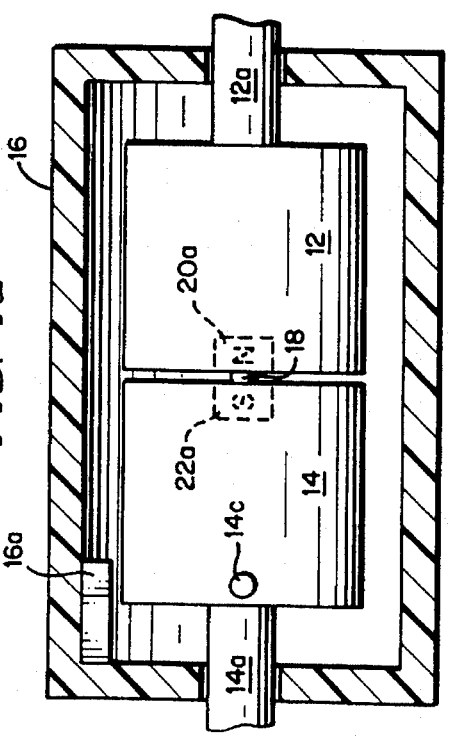

Ultimately the magnetic fields of the magnet pairs 20a, 20b and 22a, 22b will again be positioned relative to one another so as to be in a state of mutual attraction. That is, as shown in FIGS. 3d and 4d, magnets 20b, 22a and 20a, 22b are becoming paired such that magnets 20b and 20a attract magnets 22a and 22b, respectively, and vice versa. As a result of this mutual magnetic attraction in the state shown in FIGS. 3d and 4d, the distal hub 14 will rotate in a direction counter to the rotation direction of the proximal hub 12 until the magnets 20b, 22a on the one hand, and magnets 20a, 22b on the other hand oppose one another (i.e., assume the state as shown in FIG. 3a). Once the magnets 10b, 22a and 20a, 22b oppose one another, the rotation direction of the distal hub 14 will again reverse so that the hub 14 rotates in the same direction as the proximal hub 12. This process repeats itself during subsequent rotational cycles to cause the distal hub 14 to undergo rotary oscillations.

The discussion above with respect to FIGS. 2, 3a–3d and 4a–4d focussed upon opposite poled magnet pairs 20a, 22a and 20b, 22b since opposite poled magnets presently represent a particularly preferred embodiment of this invention. However, these magnet pairs 20a, 22a and 20b, 22b could likewise be formed of like (not opposite) poles, in which case the magnetic repulsion of one of the magnets in the pairs 20a, 22a and 20b, 22b would influence the rotation direction of the other magnet in the pairs 20a, 22a and 20b, 22b causing rotation direction reversal, and hence oscillation, to occur in one of the hubs 12 or 14.

The stop element 16a described previously represents an exemplary structural element according to the present invention which serves to magnetically decouple the magnet pairs 20a, 22a and 20b, 22b as described above. Thus, according to the present invention, a compliant stop element may be employed which could be embodied in several structural forms. For example, as shown schematically in FIG. 1, a compliant stop element in the form of a tension or compression spring 30 (depending upon the placement of the spring 30 relative to the rotation direction of the hub 14 and its shaft 14a) may be provided alternatively (or additionally) to the stop element 16a described previously. If a tension or compression spring 30 is provided, it preferably will be positioned so as to exert a tangential bias force against the hub shaft 14a so as to assist in decoupling of the magnet pairs 20a, 22a and 20b, 22b (i.e., when the force of the spring 30 exceeds the magnetic force of the magnet pairs 20a, 22a and 20b, 22b). Thus, as shown schematically in FIG. 2, the spring 30 extends tangentially from spring boss 30a to housing boss 30b.

The compliant stop element may, however, be embodied in torsional springs which serve to exert a torsion force on the hub 14 causing decoupling of the magnet pairs 20a, 22a and 20b, 22b. The compliant stop may thus be a torsion rod concentric to the shaft 14a and/or a conventional torsion spring element. Furthermore, the stop element 16a may itself inherently provide compliant functions. That is, the stop element 16a may be formed of an elastomeric material which serves to provide sufficient rebound force when struck by the boss 14c. Thus, as used herein and in the accompanying claims, the term "stop element" and like terms are meant to refer to any structure or combination of structures which serves to magnetically decouple the paired magnets. Thus, the stop element according to the present invention may be embodied in a rigid stop (e.g., as by stop element 16a which is contacted by boss 14c, or may be embodied in a compliant stop (e.g., as by a spring element such as a compression, tension or torsion spring and/or the inherent resiliency of stop 16a if formed of an elastomeric material).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An oscillatory coupling comprising:

a pair of opposed hubs rotatable independently about a common axis;

a housing which houses said pair of opposed hubs;

a pair of permanent magnets, one of said magnets being carried by one of said hubs, and the other of said magnets being carried by the other of said hubs; and said housing includes a stop element for arresting rotation of said other hub in a selected rotation direction.

2. The oscillatory coupling as in claim 1, wherein said stop element is rigid.

3. The oscillatory coupling as in claim 1, wherein said stop element is a compliant stop element.

4. The oscillatory coupling as in claim 3, wherein said compliant stop element is a spring.

5. The oscillatory coupling as in claim 3, wherein said compliant stop element is formed of an elastomeric material.

6. The oscillatory coupling as in claim 1, which includes a support shaft defining said common axis and coaxially joining said opposed hubs to allow for independent rotation thereof about said common axis.

7. The oscillatory coupling as in claim 1, which includes at least one pair of like poled magnets.

8. The oscillatory coupling as in claim 7, which includes two pairs of said like poled magnets.

9. A surgical instrument which comprises:
   a motor;
   a surgical implement for performing surgery on tissue; and
   a coupling unit for coupling said motor to said surgical implement so as to impart rotary oscillatory motion to said surgical implement, said coupling unit including;
   (i) a pair of opposed hubs rotatable independently about a common axis, one of said hubs being connected to said motor so as to be continuously driven thereby in a selected rotation direction;
   (ii) a pair of permanent magnets, one of said magnets being carried by said one hub, and the other of said magnets being carried by the other of said hubs; and
   (iii) a stop element for arresting rotation of said other hub in said selected rotation direction, and allowing said other hub to rotate in a direction opposite said selected rotation direction, whereby oscillatory motion is imparted to said surgical implement.

10. The surgical instrument as in claim 9, wherein said pair of permanent magnets are oppositely poled, and wherein,
   (a) alignment of said pair of magnets couples said other hub magnetically to said one hub so that said one and other hubs rotate concurrently in said selected rotation direction through a first portion of a rotation cycle of said one hub until said other hub contacts said stop element which thereby magnetically uncouples said aligned magnets, and wherein
   (b) continued rotation of said one hub in said selected rotation direction through a second portion of said rotation cycle brings said one magnet carried thereby into magnetic proximity with said other magnet carried by said other hub to thereby responsively cause said other hub to rotate in a direction reverse to said selected rotation direction of said one hub until said pair of magnets are again aligned at which time said other hub again reverses rotation direction so that said one and other hubs rotate concurrently in said selected rotation direction, whereby said other hub oscillates between said selected rotation direction and said reverse rotation direction.

11. The surgical implement as in claim 9, which includes a support shaft defining said common axis and coaxially joining said opposed hubs to allow for independent rotation thereof about said common axis.

12. The surgical instrument as in claim 9, wherein said coupling includes a housing which houses said one and other hubs, and wherein said stop element includes a boss protruding from said other hub which contacts said housing and arrests rotation of said other hub in said selected rotation direction.

13. The surgical instrument as in claim 9, which includes two pairs of opposite poled magnets.

14. The surgical instrument as in claim 9, wherein said magnets have like poles.

15. The surgical instrument as in claim 14, which includes two pairs of like poled permanent magnets.

16. A method of effecting oscillatory motion comprising the steps of:
   (i) providing a pair of magnets carried respectively by one and another hubs which are rotatable independently relative to one another about a common axis;
   (ii) rotating said one hub in a selected rotation direction during a first portion of a rotation cycle to thereby cause said other hub to concurrently rotate therewith in said selected rotation direction by virtue of the magnetic field interaction of said pair of magnets;
   (iii) arresting rotational movement of said other hub in said selected rotation direction while continuing to rotate said one hub in said selected rotation direction through a second portion of said rotation cycle so as to cause the said other hub to rotate in a direction which is reverse to said selected rotation direction;
   (iv) bringing said magnet carried by said one hub into proximity with said magnet carried by said other hub during said second portion of said rotation cycle to thereby cause the rotation direction of said other hub to reverse and thereby be rotated in said selected rotation direction; and then
   (v) repeating steps (ii)–(iv) during subsequent rotation cycles to effect oscillation of said other hub between said selected and opposite rotation directions.

17. The method as in claim 16, wherein step (iii) is practiced by bringing said other hub into contact with a stop element.

18. The method as in claim 16, wherein said one and other magnets have either opposite or like poles.

19. The oscillatory coupling as in claim 18, wherein said stop means is a rigid stop element.

20. An oscillatory coupling comprising:
   a pair of opposed hubs rotatable independently about a common axis;
   a housing which houses said pair of opposed hubs;
   a pair of permanent magnets, one of said magnets being carried by one of said hubs, and the other of said magnets being carried by the other of said hubs; and
   said housing includes stop means for arresting rotation of said other hub in a selected rotation direction to magnetically decouple said pair of permanent magnets.

21. The oscillatory coupling as in claim 20, wherein
   said one hub is continuously rotatable in said selected rotation direction such that said one magnet responsively drives said other magnet in one direction during a portion of the rotation of said one hub in said selected direction until rotation of said other hub is arrested by said stop means at which time said other hub rotates in a direction opposite to said one hub, and wherein
   continued rotation of said one hub in said selected rotation direction will again bring said one magnet into proximity with said other magnet so that the rotation direction of said other hub will again reverse and be rotated in said selected rotation direction, whereby oscillatory motion is imparted to said other hub.

22. The oscillatory coupling as in claim 20, wherein said stop means includes a compliant stop element.

23. The oscillatory coupling as in claim 22, wherein said compliant stop element is formed of an elastomeric material.

24. The oscillatory coupling as in claim 22, wherein said compliant stop element is a spring.

25. An oscillatory coupling comprising:

a pair of opposed hubs rotatable independently about a common axis;

a housing which houses said pair of opposed hubs;

a pair of permanent magnets, one of said magnets being carried by one of said hubs, and the other of said magnets being carried by the other of said hubs; and a stop element for arresting rotation of said other hub in a selected rotation direction, wherein said one hub is continuously rotatable in said selected rotation direction such that said one magnet responsively drives said other magnet in one direction during a portion of the rotation of said one hub in said selected direction until rotation of said other hub is arrested by said stop element at which time said other hub rotates in a direction opposite to said one hub, and wherein continued rotation of said one hub in said selected rotation direction will again bring said one magnet into proximity with said other magnet so that the rotation direction of said other hub will again reverse and be rotated in said selected rotation direction, whereby oscillatory motion is imparted to said other hub.

26. The oscillatory coupling as in claim 25, which includes at least one pair of like poled magnets.

27. The oscillatory coupling as in claim 26, which includes two pairs of said like poled magnets.

28. The oscillatory coupling as in claim 25, wherein said one and another magnets have either like or opposite poles.

29. An oscillatory coupling comprising:

a pair of opposed hubs rotatable independently about a common axis; a housing which houses said pair of opposed hubs;

a pair of oppositely poled permanent magnets, one of said magnets being carried by one of said hubs, and the other of said magnets being carried by the other of said hubs; and said housing includes a stop element for arresting rotation of said other hub in a selected rotation direction, wherein alignment of said pair of magnets couples said other hub magnetically to said one hub so that said one and other hubs rotate concurrently in said selected rotation direction through a first portion of a rotation cycle of said one hub until said other hub contacts said stop element which thereby magnetically uncouples said aligned magnets, and wherein continued rotation of said one hub in said selected rotation direction through a second portion of said rotation cycle brings said one magnet carried thereby into magnetic proximity with said other magnet carried by said other hub to thereby responsively cause said other hub to rotate in a direction reverse to said selected rotation direction of said one hub until said pair of magnets are again aligned at which time said other hub again reverses rotation direction so that said one and other hubs rotate concurrently in said selected rotation direction, whereby said other hub oscillates between said selected rotation direction and said reverse rotation direction.

30. The oscillatory coupling as in claim 25 or 29, which includes a support shaft defining said common axis and coaxially joining said opposed hubs to allow for independent rotation thereof about said common axis.

31. An oscillatory coupling comprising:

a pair of opposed hubs rotatable independently about a common axis;

a housing which houses said pair of opposed hubs;

a pair of permanent magnets, one of said magnets being carried by one of said hubs, and the other of said magnets being carried by the other of said hubs; and a stop element for arresting rotation of said other hub in a selected rotation direction, wherein said stop element includes a boss protruding from said other hub which contacts said housing and arrests rotation of said other hub in said selected rotation direction.

32. An oscillatory coupling comprising:

a pair of opposed hubs rotatable independently about a common axis;

a housing which houses said pair of opposed hubs;

at least one pair of oppositely poled permanent magnets, one of said magnets being carried by one of said hubs, and the other of said magnets being carried by the other of said hubs; and said housing includes a stop element for arresting rotation of said other hub in a selected rotation direction.

33. The oscillatory coupling as in claim 32, which includes two pairs of said oppositely poled magnets.

* * * * *